US00PP26761P2

(12) United States Plant Patent
Hurd

(10) Patent No.: US PP26,761 P2
(45) Date of Patent: May 24, 2016

(54) ***HEUCHERA* PLANT NAMED 'LAVA LAMP'**

(50) Latin Name: ***Heuchera* spp.**
Varietal Denomination: Lava Lamp

(71) Applicant: Kevin A. Hurd, Merrillville, IN (US)

(72) Inventor: Kevin A. Hurd, Merrillville, IN (US)

(73) Assignee: Walters Gardens, Inc, Zeeland, MI (US)

( * ) Notice: Subject to any disclaimer, the term of this patent is extended or adjusted under 35 U.S.C. 154(b) by 257 days.

(21) Appl. No.: 13/998,787

(22) Filed: Dec. 6, 2013

(51) Int. Cl.
*A01H 5/12* (2006.01)

(52) U.S. Cl.
USPC ..... Plt./440

(58) Field of Classification Search
USPC ..... Plt./440
See application file for complete search history.

(56) References Cited

U.S. PATENT DOCUMENTS

PP13,288 P2 * 11/2002 Heims ..... Plt./440

* cited by examiner

*Primary Examiner* — June Hwu

(57) ABSTRACT

The new and distinct plant hybrid cultivar *Heuchera* 'Lava Lamp' with large, billowy mass of very large, coppery-purple leaves with deep purple undersides. The newest leaves emerge a coppery-purple and then deepen to purplish-green as they age. This variety has large, flat, rounded, shallowly-lobed leaves. Deep purple scapes carry plump wands of closely-spaced cream and maroon-colored flowers in early summer.

2 Drawing Sheets

Botanical denomination: *Heuchera* spp.
Variety designation: 'Lava Lamp'.

BACKGROUND OF THE INVENTION

The present invention relates to a new and distinct cultivar of Coral Bells in the Saxifragaceae family and given the cultivar name of 'Lava Lamp'. *Heuchera* 'Lava Lamp' is a hybrid crossed by Kevin A. Hurd on Apr. 24, 2009 between *Heuchera* 'Encore' U.S. Plant Pat. No. 19,578 with *Heuchera* 'Mocha' U.S. Plant Pat. No. 18,386. Both parents involved the species *Heuchera villosa* in at least part of the genetic background, but complete ancestry of the female and male parents is unknown. The cross was performed at a perennial nursery in Zeeland, Mich., USA. The seed was harvested on May 6, 2009. The resultant individual plant was evaluated with hundreds of other crosses and thousands of other seedlings and assigned the breeder code K9-38-01. The new plant passed final evaluation in the summer of 2012. *Heuchera* 'Lava Lamp' has been asexually propagated by division at the same nursery in Zeeland, Mich. and also by careful tissue culture propagation, and the resultant plants have remained stable, true to type and exhibit the same characteristics as the original plant for multiple generations. *Heuchera* 'Lava Lamp' is useful in arrangements as a cut flower or foliage, or in the landscape as a specimen, en masse, or in containers.

BRIEF SUMMARY OF THE INVENTION

In comparison to the female parent, 'Encore', the new plant has rounder leaf blades, no purple silver overlay and vein color width and less acute leaf lobe apices. Compared to the male parent, 'Mocha', the new plant has slightly smaller less dissected and rounder leaves with more coppery coloring than the dark purple of 'Mocha'.

The nearest comparison varieties are *Heuchera* 'Bella Notte' U.S. Plant Pat. No. 24,291, 'Black Beauty' U.S. Plant Pat. No. 13,288, 'Blackout' U.S. Plant Pat. No. 20,613, 'Creole Nights' U.S. Plant Pat. No. 24,087, 'Galaxy' U.S. Plant Pat. No. 24,574 and 'Gotham' U.S. Plant Pat. No. 24,290 and 'Rio' U.S. Plant Pat. No. 24,273.

TABLE 1

| Cultivar | Leaf Blade Color | Leaf Surface | Leaf Texture | Lobe Apex | Leaf Dissection | Flower Color |
|---|---|---|---|---|---|---|
| 'Bella Notte' | maroon-black | glossy | flat | rounded | minimal | pink |
| 'Black Beauty' | black-red | glossy | ruffled | rounded | moderate | light cream |
| 'Blackout' | black-brown | glossy | flat | acute | moderate | cream |
| 'Creole Nights' | black-purple | glossy | flat | rounded | moderate | white |
| 'Galaxy' | brown-red | semi-glossy | flat | acute | moderate-high | white |
| 'Gotham' | black-purple w/slight silver | matte | flat | rounded | moderate | light yellow |
| 'Lava Lamp' | copper-purple | matte | flat | rounded | minimum-moderate | cream and maroon |
| 'Rio' | red-amber w/silver | matte | flat | acute | moderate | white |

*Heuchera* 'Lava Lamp' is unique from its parents and all the above listed Coral Bells cultivars and all others known to the inventor in the following combined traits:

1. Foliage with large, rounded, flat blades with matte surface above and slightly glossy deep purple below.
2. Foliage of changing coloration starting the spring emerging a light coppery-purple and darkening to a purplish-green later in season.

3. The closely-spaced, cream and maroon-colored, campanulate flowers appear on widely branched panicles effective over a long period beginning late spring.
4. The new plant has a vigorous and billowy habit and tolerates heat and humidity.

BRIEF DESCRIPTION OF THE DRAWINGS

The photograph of the new plant demonstrates the overall appearance of the plant including the unique traits. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
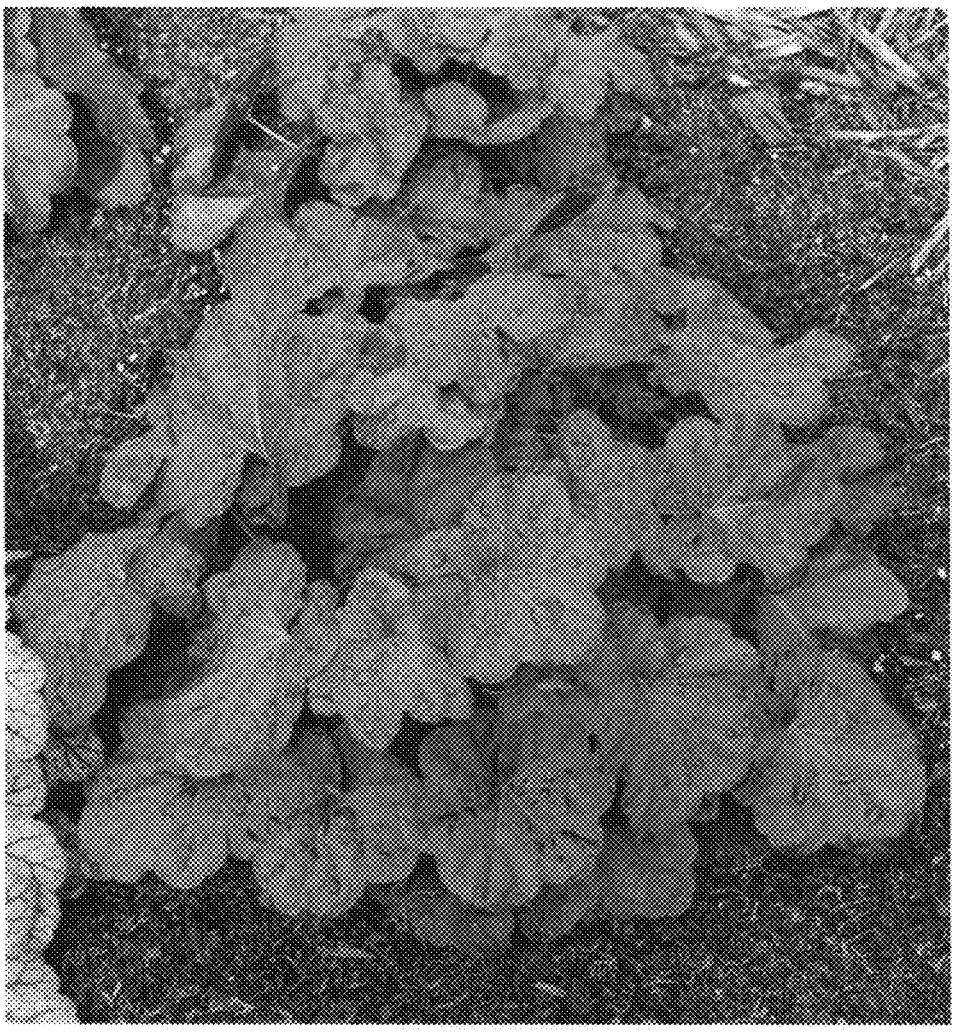
FIG. 1 shows habit and foliage of the new plant prior to flowering in late September.
Figure 2:
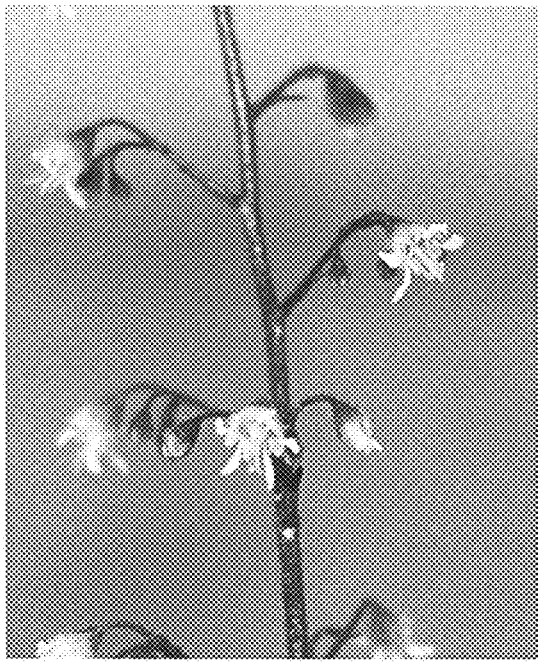
FIG. 2 shows a close-up of flowers on a repeat panicle in late July.
Figure 3:
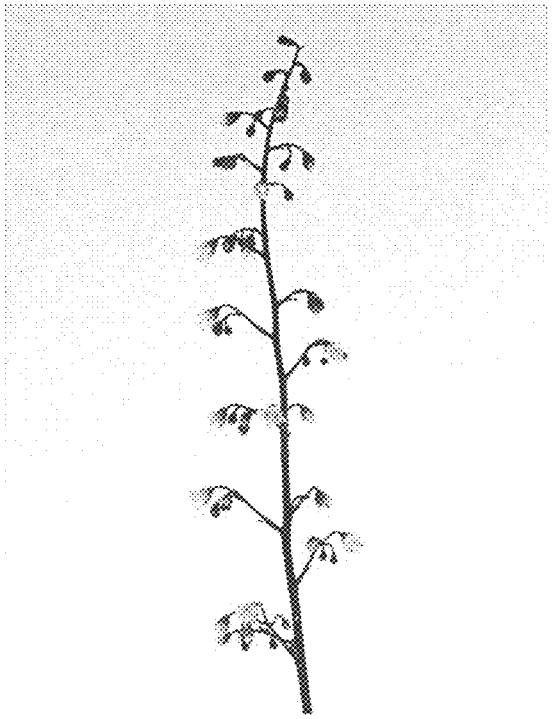
FIG. 3 shows a repeat panicle in late July.

The following description is based on a two-year old plant growing in a lightly shaded greenhouse in Zeeland, Mich., USA. A one-year old plant grown in a shaded trial garden with supplemental water and fertilizer was also used for further descriptions of late winter or early spring foliage colors. The new plant has not been grown under all possible environmental conditions and may phenotypically appear different under different conditions such as light, temperature, fertilizer, and water, without any difference in genotype. The color descriptions used are from the 2001 edition of The Royal Horticultural Society Colour Chart except where common dictionary terms are used.

Parentage: Female (seed parent)—*Heuchera* 'Encore' U.S. Plant Pat. No. 18,578; male (pollen)—*Heuchera* 'Mocha', U.S. Plant Pat. No. 18,386.

Plant habit: Hardy herbaceous perennial with basal rosette of foliage; mounded foliage about 28 cm tall and 40 cm in diameter; about 120 leaves densely packed leaves per plant.

Roots: Fibrous, finely branched.

Growth rate: Rapid, rooting from cutting in two weeks and finishing in three-liter container in about 3 months.

Foliage: Cordate to rounded, serrate, sparsely hirsutulous abaxial and adaxial, palmately lobed with up to seven main lobes each having three or more sub-lobes; blade up to about 12.5 cm long and 12.5 cm wide, average about 10.5 cm long and 10.5 cm wide; slightly undulate to convex downward, leaf color is variable with season.

Leaf color: Young spring emerging adaxial leaves between RHS 179B and RHS 179C, young spring emerging abaxial leaves between RHS N186D and RHS N77B; mid-season flowering time leaves adaxial nearest RHS N175A with veins nearest RHS 183B; abaxial mid-season leaves nearest RHS 187C; late season and fall adaxial foliage nearest RHS 184B with nearest RHS 187A bleeding out from the minor veins, late season and fall abaxial foliage between RHS N186C and RHS N186D; adaxial winter and early spring leaves nearest RHS N189A with over lay of RHS N187A and abaxial winter and early spring leaves between RHS N186B and RHS N186C.

Leaf margin: Hirsutulous with lobules finely fimbricate to mucronate at apices.

Leaf apex: Rounded, hirsutulous.

Leaf base: Cordate, auriculate with overlapping lobes.

Leaf surface: Sparsely hirsutulous abaxial and adaxial; adaxial slightly vernicose when young in spring, matte when mature; abaxial vernicose all season.

Leaf quantity: Dense, about 120 per plant.

Veins: Palmate, sparsely hirsutulous; ridged abaxial.

Vein color: On emerging spring foliage adaxial nearest RHS 186C from base to about half way to margin and same as the surrounding tissue to the margin; veins on emerging spring foliage abaxial nearest RHS 71B; adaxial mid-season flowering time nearest RHS 187C, abaxial between RHS 71B and RHS 71A; winter adaxial nearest RHS 185D and RHS N199D with tinting of RHS 185D at base, with abaxial nearest RHS N77B.

Petiole: Cylindrical, moderately vernicose, sparsely hirsutulous; up to about 14.5 cm long and 3.0 mm wide.

Petiole color: Ranging from between RHS N186C and RHS N186D with region under leaf blade lightening to between RHS 186A and RHS 186B.

Inflorescence: Nearly-vertical open panicle with branched cymose subaxes, one panicle per main division; numerous flowers per panicle; flowering starting in late spring to early summer lasting for about 3 weeks; no significant fragrance detected; medium density on panicle, about 85 cm long and spreading to about 6.5 cm diameter; about 150 flowers per panicle.

Peduncle: Stiff, cylindrical, densely hirsutulous, about 80 to 90 cm long and 3 mm in diameter at base; attitude upright to nearly vertical.

Peduncle color: Nearest RHS 187A.

Pedicel: Cylindrical, hirsutulous, about 2.5 mm long and 0.5 mm diameter.

Pedicel color: Nearest RHS 187B.

Flower bud one day prior to opening: Ovoid; glandular; about 3.0 mm long and 2.5 mm diameter, bluntly acute apex and tapered base.

Bud color: Nearest RHS 187B one day prior to opening.

Flower: Perfect, campanulate, actinomorphic; individual flowers lasting about 4 days on plant or as cut flower; about 7.0 mm across and about 7.0 mm long; attitude semi-downwards between 15 to 45 degree below horizontal.

Calyx: Five, apex acute, base fused in proximal half to form hypanthium; individually about 4.0 mm long and 2.0 mm across at point of fusion.

Calyx color: Tinted nearest RHS 187B near base, lightening to nearest RHS59C distally with a margin of about 0.5 mm of nearest RHS N155D.

Petals: Five, oblanceolate, acute apex and tapered base, entire, recurved to about 160 degrees from side of flower to point toward back of flower.

Petal color: While opening nearest RHS 62D; when fully opened white, lighter than RHS 155D, ageing to nearest RHS 158D before dehiscing.

Androecium:

*Filaments*.—Five, thin, about 5.0 mm long and less than 0.5 mm diameter; color lighter than RHS 62D.

*Anther*.—Oblong, about 0.5 mm long and 0.25 mm across; color nearest RHS 25A.

*Pollen*.—Sparse; color nearest RHS 17B.

Gynoecium: Two-beaked; bifid style with pistil split at ovary; about 6.0 mm long.

*Ovary*.—Half-inferior; color nearest RHS 63D.

*Style*.—Two, split apart at apex of ovary; color nearest RHS 62D at base and nearest RHS N155D at apex.

*Stigma*.—Smaller than 0.5 mm diameter, globose; color light pink nearest RHS 63C.

Fruit: Two-beaked capsule, about 6 mm long and 3 mm in diameter at widest portion; color nearest RHS 199A when mature.

Seed: Ovoid, less than 1 mm long and wide; color black, nearest RHS 202A.

Disease and pest resistance: The new plant grows best with ample moisture and drainage in either sun or shade. It is more tolerant of hot and humid environments than typical Coral Bells. Cold hardy from USDA zones 4 to 9. Other resistance and tolerance beyond that normal for *Heuchera* has not been observed.

I claim:

1. A new and distinct Coral Bells plant named *Heuchera* 'Lava Lamp' as herein described and illustrated with foliage of light coppery-purple, darkening to a purplish-green later in the season, and very deep purple underside, with cream and maroon-colored flowers and with improved heat and humidity tolerance.

* * * * *